(12) United States Patent
Cha et al.

(10) Patent No.: US 11,840,921 B2
(45) Date of Patent: Dec. 12, 2023

(54) DETECTING CARBON DIOXIDE LEAKAGE IN THE FIELD

(71) Applicant: Saudi Arabian Oil Company, Dhahran (SA)

(72) Inventors: Dong Kyu Cha, Dhahran (SA); Mohammed Badri AlOtaibi, Al Khobar (SA); Subhash Chandrabose Ayirala, Dhahran (SA); Ali Abdallah Al-Yousef, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 172 days.

(21) Appl. No.: 17/249,461

(22) Filed: Mar. 2, 2021

(65) Prior Publication Data
US 2022/0282613 A1    Sep. 8, 2022

(51) Int. Cl.
*E21B 43/16*    (2006.01)
*E21B 47/113*   (2012.01)
*B82Y 30/00*    (2011.01)

(52) U.S. Cl.
CPC .......... *E21B 47/113* (2020.05); *E21B 43/164* (2013.01); *B82Y 30/00* (2013.01)

(58) Field of Classification Search
CPC ...... E21B 47/113; E21B 43/164; E21B 43/16; E21B 49/00; B82Y 30/00; Y02A 50/20;
(Continued)

(56) References Cited

U.S. PATENT DOCUMENTS

| 5,191,557 A | 3/1993 | Rector et al. |
| 7,326,931 B2 | 2/2008 | Frodl et al. |

(Continued)

FOREIGN PATENT DOCUMENTS

| CN | 112236144 A | * | 1/2021 | ........... B01D 53/228 |
| EP | 3203221 A1 | * | 8/2017 | ........... G01N 21/359 |

(Continued)

OTHER PUBLICATIONS

Catalog Cut for Whatman Anodisc inorganic filter membrane, WHA68096002; as seen in IDS (Year: 2022).*

(Continued)

*Primary Examiner* — Tarun Sinha
*Assistant Examiner* — James I Burris
(74) *Attorney, Agent, or Firm* — Fish & Richardson P.C.

(57) ABSTRACT

Methods for fabricating a sensor module for detecting carbon dioxide leakage from a subsurface reservoir are disclosed. The methods include attaching anodic aluminum oxide porous membrane onto a first conductive electrode to form an anodic aluminum oxide template; initiating growth of a plurality of $TiO_2$ nanotubes inside the AAO template using an atomic layer deposition process; removing the anodic aluminum oxide template from the first metal electrode leaving the plurality of $TiO_2$ nanotubes on the first conductive electrode; attaching a second conductive electrode to the plurality of $TiO_2$ nanotubes; connecting the first and the second conductive electrodes with an electric line to form a sensor; providing a rollable sheet of non-conductive material; and attaching a plurality of sensors to the rollable sheet of non-conductive material forming the sensor module.

17 Claims, 6 Drawing Sheets

(58) Field of Classification Search
CPC .. G01N 27/127; G01N 27/12; G01N 33/0031; G01N 33/00; G01N 33/004
See application file for complete search history.

(56) References Cited

U.S. PATENT DOCUMENTS

| | | |
|---|---|---|
| 7,704,746 B1 | 4/2010 | White et al. |
| 8,297,351 B2 | 10/2012 | Yoshiuchi et al. |
| 8,377,730 B2 | 2/2013 | Yang et al. |
| 8,466,799 B2 | 6/2013 | Kim et al. |
| 9,562,430 B1 | 2/2017 | Monteiro |
| 10,090,531 B2 | 10/2018 | Cerri et al. |
| 10,677,046 B2 | 6/2020 | Mohaghegh et al. |
| 10,705,047 B2 | 7/2020 | Mohanty et al. |
| 11,002,718 B2 | 5/2021 | Schwartz et al. |
| 11,008,816 B2 | 5/2021 | Zhan et al. |
| 2005/0224360 A1 | 10/2005 | Varghese et al. |
| 2008/0224717 A1 | 9/2008 | Kim et al. |
| 2011/0015874 A1 | 1/2011 | Song et al. |
| 2011/0283821 A1* | 11/2011 | Ober ............... G01N 33/0031 73/866.1 |
| 2012/0039668 A1 | 2/2012 | Park et al. |
| 2012/0092960 A1 | 4/2012 | Gaston et al. |
| 2012/0111093 A1 | 5/2012 | Brahim et al. |
| 2013/0108865 A1 | 5/2013 | Boulanger et al. |
| 2014/0002089 A1 | 1/2014 | Wood et al. |
| 2014/0291591 A1 | 10/2014 | Jeon et al. |
| 2016/0003770 A1 | 1/2016 | Klootwijk et al. |
| 2017/0268338 A1 | 9/2017 | Qin et al. |
| 2017/0285211 A1 | 10/2017 | Monteiro et al. |
| 2017/0292376 A1 | 10/2017 | Kumar et al. |
| 2018/0224391 A1 | 8/2018 | Choa et al. |
| 2021/0372270 A1 | 12/2021 | Gooneratne et al. |

FOREIGN PATENT DOCUMENTS

| | | |
|---|---|---|
| EP | 2572187 | 7/2020 |
| KR | 101301953 | 8/2013 |
| TW | 201743031 | 12/2017 |

OTHER PUBLICATIONS

Gaslab Pro CO2 Enginer K30 Sensor Module Manual (Year: 2022).*

Vardan et al. (TiO2 Nanotubes: Recent Advances in Synthesis and Gas Sensing Properties, www.mdpi.com/journal/sensors, Oct. 31, 2013 (Year: 2013).*

PCT International Search Report and Written Opinion in International Appln. No. PCT/US2022/018359, dated Aug. 19, 2022.

PCT International Search Report and Written Opinion in International Appln. No. PCT/US2022/018361, dated Jul. 29, 2022, 19 pages.

U.S. Appl. No. 17/190,271, Cha et al., filed Mar. 2, 2021.

Beaubien et al., "Monitoring of near-surface gas geochemistry at the Weyburn, Canada, CO2-EOR site, 2001-2011," International Journal of Greenhouse Gas Control, Elsevier Ltd., Jun. 2013, 16(1):S236-S262, 27 pages.

Galstyan et al., "TiO2 Nanotubes: Recent Advances in Synthesis and Gas Sensing Properties," Sensors, Oct. 2013, 13(11): 14813-14838, 26 pages.

Maziarz et al., "Nanostructured TiO2-based gas sensors with enhanced sensitivity to reducing gases," Beilstein Journal of Nanotechnology, Nov. 2016, 7:1718-1726, 9 pages.

Sigmaaldrich.com [online], "Whatman® Anodisc inorganic filter membrane" Nov. 2015, [retrieved on May 13, 2021], retrieved from: URL <https://www.sigmaaldrich.com/catalog/product/aldrich/wha68096002?lang=en&region=US>, 2 pages.

PCT International Invitation to Pay Additional Fees in International Appln. No. PCT/US2022/018361, dated Jun. 8, 2022, 13 pages.

PCT International Invitation to Pay Additional Fees in International Appln. No. PCT/US2022/018359, dated Jun. 28, 2022, 13 pages.

* cited by examiner

TOP VIEW OF TiO$_2$ NANOTUBES ON THE ELECTRODE

DETECTING CARBON DIOXIDE LEAKAGE IN THE FIELD

TECHNICAL FIELD

The present disclosure generally relates to methods and systems for detecting carbon dioxide leakage in an underground oil-reservoir environment, more particularly, using a sensor module with titanium dioxide ($TiO_2$) nanotubes.

BACKGROUND

Carbon dioxide is a major contributor to the greenhouse effect and global warming. Carbon dioxide injection into subsurface rocks also serves as a method to enhanced oil recovery (EOR) because it is miscible with crude oil and more economical than other similar miscible fluids. During the implementation of carbon dioxide EOR projects in the field, the injected carbon dioxide is stored underground and provides the additional benefit for carbon dioxide sequestration. Therefore, it helps to reduce the amount of carbon dioxide in the atmosphere and assists to mitigate high levels of global warming.

SUMMARY

This specification describes devices, systems, and methods for fabricating and using a sensor module to detect carbon dioxide leakage from a subsurface formation (e.g., underground oil-reservoir environment). Continuous monitoring of carbon dioxide allows reduction of carbon dioxide leakage from the reservoir to the surface. Titanium dioxide ($TiO_2$)-based sensors is one example used for carbon dioxide sensing applications. The method allows the fabrication of a sensor module with a one-dimensional structure attached to a sheet of non-conductive material with a rollable surface. In some implementations, the method allows fabrication of a sensor module with a one-dimensional structure attached on a rollable sheet of non-conductive material and installed in a subsurface formation. In some implementations, the method allows fabrication of a sensor module with a one-dimension structure attached to a drill rig and installed in a subsurface formation (e.g., shallow wells in the carbon dioxide project area). The sensor module can include a plurality of sensors and a communication device. Each sensor from the plurality of sensors includes a first conductive electrode, a second conductive electrode, and a plurality of $TiO_2$ nanotubes. The conductive electrodes are connected with an electric line.

These devices, systems, and methods fabricate a sensor module attached to a rollable surface that allows ease of installation, transfer, and usage at the field sites.

In some aspects, a method for fabricating a sensor module for detecting carbon dioxide leakage from a subsurface reservoir includes attaching an anodic aluminum oxide porous membrane onto a first conductive electrode to form an anodic aluminum oxide template; initiating growth of a plurality of $TiO_2$ nanotubes inside the anodic aluminum oxide template using an atomic layer deposition process; removing the anodic aluminum oxide template from the first metal electrode leaving the plurality of $TiO_2$ nanotubes on the first conductive electrode; attaching a second conductive electrode to the plurality of $TiO_2$ nanotubes; connecting the first and the second conductive electrodes with an electric line to form a sensor; providing a rollable sheet of non-conductive material, the sheet having a width between 50 cm and 2 m, a height between 50 cm and 2 m, and a thickness between 5 and 10 cm; and attaching a plurality of the sensors to the rollable sheet of non-conductive material to form the sensor module.

In some aspects, a method for detecting a carbon dioxide leakage from a subsurface reservoir includes deploying a sensor module above the subsurface reservoir, the sensor module includes a rollable sheet of non-conductive material; monitoring a carbon dioxide concentration by noting an electrical resistance using the sensor module; detecting carbon dioxide leakage upon an increase in the electrical resistance; reporting the carbon dioxide leakage to the surface using the sensor module; and removing the sensor module from the subsurface.

Embodiments of the methods for fabricating a sensor module for detecting carbon dioxide leakage from a subsurface reservoir can include one or more of the following features.

In some embodiments, the sensor includes an electrical resistance sensor.

In some embodiments, the method includes covering of each sensor from the plurality of sensors with a protective cover to prevent contamination.

In some embodiments, the method includes unrolling the sensor module.

In some embodiments, the method includes placing the sensor module on a ground surface.

In some aspects, a sensor module for detecting carbon dioxide leakage in a subsurface reservoir includes a rollable sheet of non-conductive material with a rollable surface, wherein the rollable surface includes a width between 50 cm and 2 m, a height between 50 cm and 2 m, and a thickness between 5 and 10 cm; a plurality of sensors including a first conductive electrode, a second conductive electrode, and a plurality of $TiO_2$ nanotubes, and an electric line located between and connecting the first and the second conductive electrodes. Each of the plurality of sensors is attached to the rollable sheet of non-conductive material; and a communication device communicably connected to each sensor from the plurality of sensors.

Embodiments of the sensor module for evaluating a source rock sample of a subterranean reservoir can include one or more of the following features.

In some embodiments, the rollable sheet includes rubber.

In some embodiments, the sensor module includes a protective cover to prevent contamination of each sensor from the plurality of sensors before and after sensing. In some cases, the protective cover includes rubber.

In some embodiments, each sensor from the plurality of sensors has a maximum dimension between 5 and 10 cm, and a thickness between 1 and 2 cm. In some cases, each sensor from the plurality of sensors includes has a circular shape, and the maximum dimension is a diameter.

In some embodiments, the plurality of sensors are attached to the rollable sheet and are arranged in an array.

In some embodiments, the plurality of sensors are attached to the rollable sheet and arranged in a parallel configuration.

This portable sensor module can provide an improved method for $CO_2$ leakage detection in the $CO_2$-EOR project area. In some implementations, the sensor module is attached to a drill rig to monitor and detect the $CO_2$ leakage in shallow wells underground. This provides an improved method for $CO_2$ leakage detection underground and allows most of the $CO_2$ injected in EOR projects to be permanently sequestered.

These devices, systems, and methods improve existing capabilities of $CO_2$ leakage detection between the surface and the underground environment by installing the sensor module directly on a drill rig for usage in shallow wells. The sensor module notes and increases electrical resistance with high sensitivity to carbon dioxide ($CO_2$) leakage. The large surface area allows high sensitivity to electrical resistance and economical sensing solution.

The details of one or more embodiments of these methods are set forth in the accompanying drawings and the description below. Other features, objects, and advantages of these methods will be apparent from the description and drawings and from the claims.

DETAILED DESCRIPTION

This specification describes devices, systems, and methods for fabricating and using a sensor module to detect carbon dioxide leakage from a subsurface formation (e.g., underground oil-reservoir environment). Continuous monitoring of carbon dioxide allows reduction of carbon dioxide leakage from the reservoir to the surface. Titanium dioxide ($TiO_2$)-based sensors is one example used for carbon dioxide sensing applications. The method allows the fabrication of a sensor module with a one-dimensional structure attached to a sheet of non-conductive material with a rollable surface. In some implementations, the method allows fabrication of a sensor module with a one-dimensional structure attached on a rollable sheet of non-conductive material and installed in a subsurface formation. In some implementations, the method allows fabrication of a sensor module with a one-dimension structure attached to a drill rig and installed in a subsurface formation (e.g., shallow wells in the carbon dioxide project area). The sensor module can include a plurality of sensors and a communication device. Each sensor from the plurality of sensors includes a first conductive electrode, a second conductive electrode, and a plurality of $TiO_2$ nanotubes. The conductive electrodes are connected with an electric line.

These devices, systems, and methods fabricate a sensor module attached to a rollable surface that allows ease of installation, transfer, and usage at the field sites. This portable sensor module can provide an improved method for $CO_2$ leakage detection in the $CO_2$-EOR project area. In some implementations, the sensor module is attached to a drill rig to monitor and detect the $CO_2$ leakage in shallow wells underground. This provides an improved method for $CO_2$ leakage detection underground and allows most of the $CO_2$ injected in EOR projects to be permanently sequestered. These devices, systems, and methods improve existing capabilities of $CO_2$ leakage detection between the surface and the underground environment by installing the sensor module directly on a drill rig for usage in shallow wells. The sensor module notes and increases electrical resistance with high sensitivity to carbon dioxide ($CO_2$) leakage. The large surface area allows high sensitivity to electrical resistance and economical sensing solution.

Figure 1:
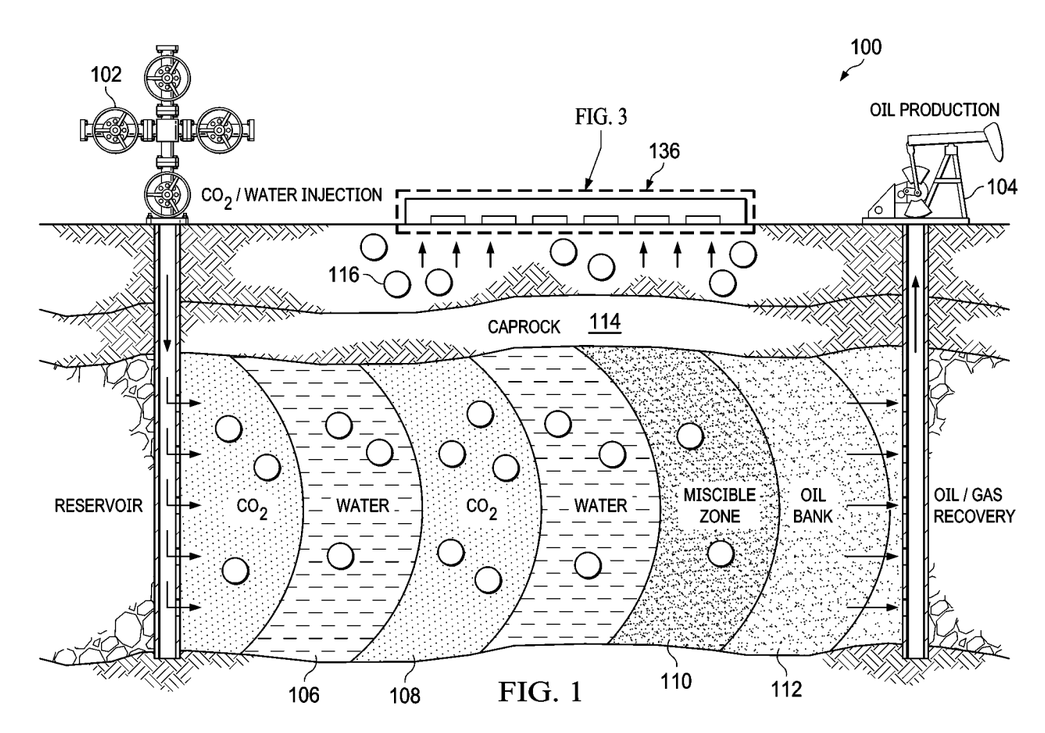
FIG. 1 is a schematic view of a subsurface reservoir including a sensor module installed on a rollable surface.

FIG. 1 is a schematic view of a subsurface reservoir 100 including the sensor module 136 installed on a rollable surface. The subsurface reservoir 100 (e.g., oil and gas reservoir) is a subsurface pool of hydrocarbons contained in porous or fractured rock formations 114. The naturally occurring hydrocarbons, such as crude oil or natural gas, are trapped by overlying rock formations 114. Carbon dioxide 108 injection 102 into subsurface rocks 114 is an example of a method used to enhance oil recovery (EOR). Carbon dioxide 108 is miscible 110 with crude oil and more economical than other similar miscible fluids. As illustrated, the carbon dioxide 108 is directed to the injection well 102 strategically placed within the pattern of wells. The injected carbon dioxide 108 enters the reservoir 100 and moves through the pore spaces of the rock 114, encountering residual droplets of crude oil, becoming miscible 110 with the oil, and forming a concentrated oil bank 112 that is swept towards the producing well 104. When the injected $CO_2$ and residual oil are miscible, the physical forces holding the two phases apart (interfacial tension) disappears. This enables the carbon dioxide 108 to displace the oil from the rock pores 114, pushing it towards the producing well 104. The oil 112 and the water 106 are pumped to the surface and directed to a centralized collection facility. The injected carbon dioxide 108 is stored underground and can provide additional benefit of carbon dioxide sequestration. To reduce carbon dioxide leakage from the reservoir to the surface, the amount of carbon dioxide leakage from the subsurface formation should be continuously monitored. The sensor module can be used to monitor gases such as water vapor, methane, nitrous oxide, ozone, and combinations thereof. In some implementations, the method allows fabrication of a sensor module with a one-dimension structure attached to a drill rig and installed in a subsurface formation (e.g., shallow wells in the carbon dioxide project area).

Figure 2:
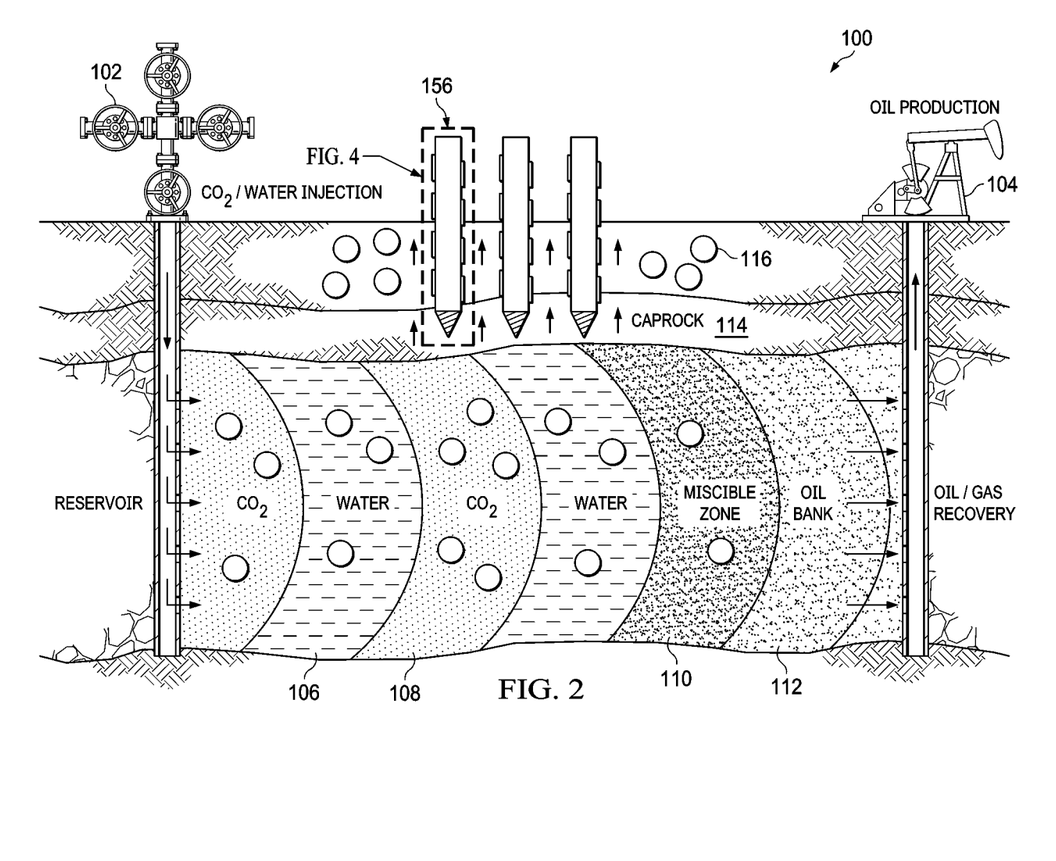
FIG. 2 is a schematic view of a subsurface reservoir including a sensor module installed on a drill rig.
Figure 3A:
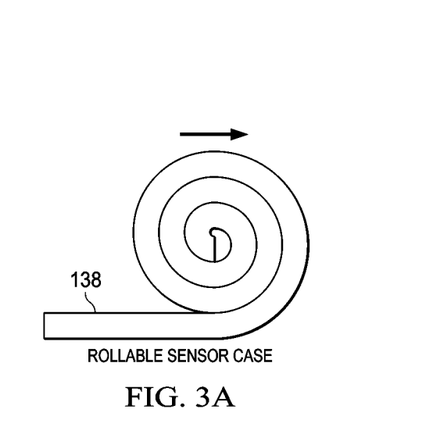
FIGS. 3A-3D are schematic views of a sensor module configuration attached on a rollable surface.
Figure 3B:
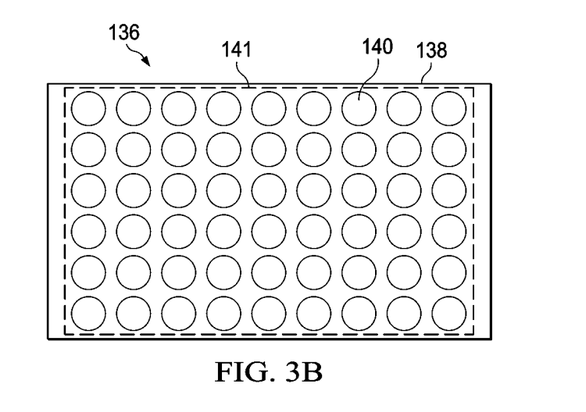
Figure 3C:
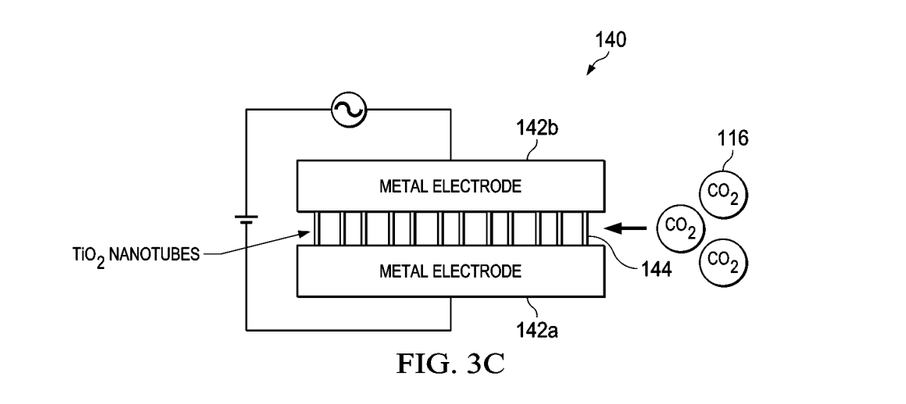
Figure 3D:
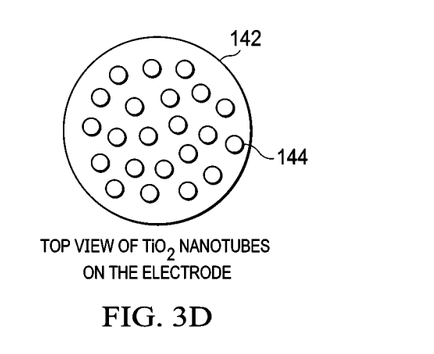

FIG. 2 is a schematic view of a subsurface reservoir 100 including the sensor module 136 installed on a drill rig 156.

FIGS. 3A-3D are schematic views of a sensor module configuration 136 attached on a rollable surface 138. The sensor module 136 can be used for detecting $CO_2$ leakage from an underground oil-reservoir environment 100. As illustrated, the sensor module 136 includes a sheet of non-conductive material with a rollable surface 138, a plurality of sensors 140, and a communication device 141. The non-conductive material includes for example, a rubber material. The rubber material is a tough elastic polymeric substance made from the latex of a tropical plant or synthetically. The rollable surface 138 has a width between 50 centimeters (cm) and 2 meters (m), a height between 50 cm and 2 m, and a thickness between 5 and 10 cm. The plurality of sensors are attached to the rollable surface and can be arranged in a series configuration. In some implementations, the plurality of sensors are attached to the rollable surface and can be arranged in a parallel configuration. Each sensor from the plurality of sensors comprises a circular shape, a diameter between 5 and 10 cm, and a thickness between 1 and 2 cm. Each sensor from the plurality of sensors 140 includes a first conductive electrode 142a, a second conductive electrode 142b, and a plurality of $TiO_2$ nanotubes 144. The conductive electrodes 142a, and 142b are connected with an electric line. Each sensor 140 is attached to the rollable surface 138 and communicably connected to the communication device 141. The sensor module 136 includes a protection cover (not shown in the figure), to prevent contamination of each sensor 140 before and after sensing. The protection cover covers all sensors and includes a flexible nonconductive material (e.g., a rubber). Each conductive electrode 142a, 142b, includes metal material. In operation, sensor module 136 can be installed at the surface. In some implementations, the sensor module 136 can be installed at a distance between the oil-reservoir 100 and the surface. The sensor module 136 observes and monitors the carbon dioxide 108 content by noting an electrical resistance. The electrical resistance increases when the sensor 140 reacts with the carbon dioxide leaked content 116. The sensor module 136 through the communication device 141 reports the carbon dioxide leaked content 116 to the surface. In some implementations, the sensors module 136 can be installed on a drill rig 156.

Figure 4:
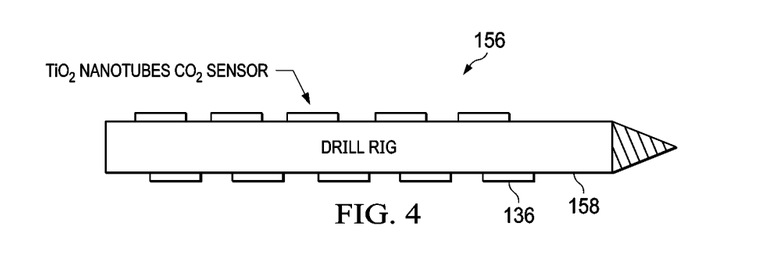
FIG. 4 is a schematic of the sensor module configuration shown in FIGS. 3A-3D installed on a drill rig.

FIG. 4 is a schematic of an example of a sensor module 136 from FIGS. 3A-3D installed on a drill rig 156. As illustrated, the sensor module 136 is attached to the outer surface of the cylindrical body 158 (e.g., drillpipe) of the drill rig 156. In some implementations, the sensor module 136 is embedded within the outer surface of the cylindrical body 158 (e.g., drillpipe) of the drill rig 156. The sensors module structure, materials, and sensitivity are the same as those described with reference to FIG. 2. In some examples, the drill rig 156 can be a mobile drill rig that includes diameter between 8.5 and 12.25 inches (in) and a length between 100 and 260 feet (ft). The plurality of sensor modules are arranged a distance apart from one another and longitudinally along the cylindrical body.

Figure 5:
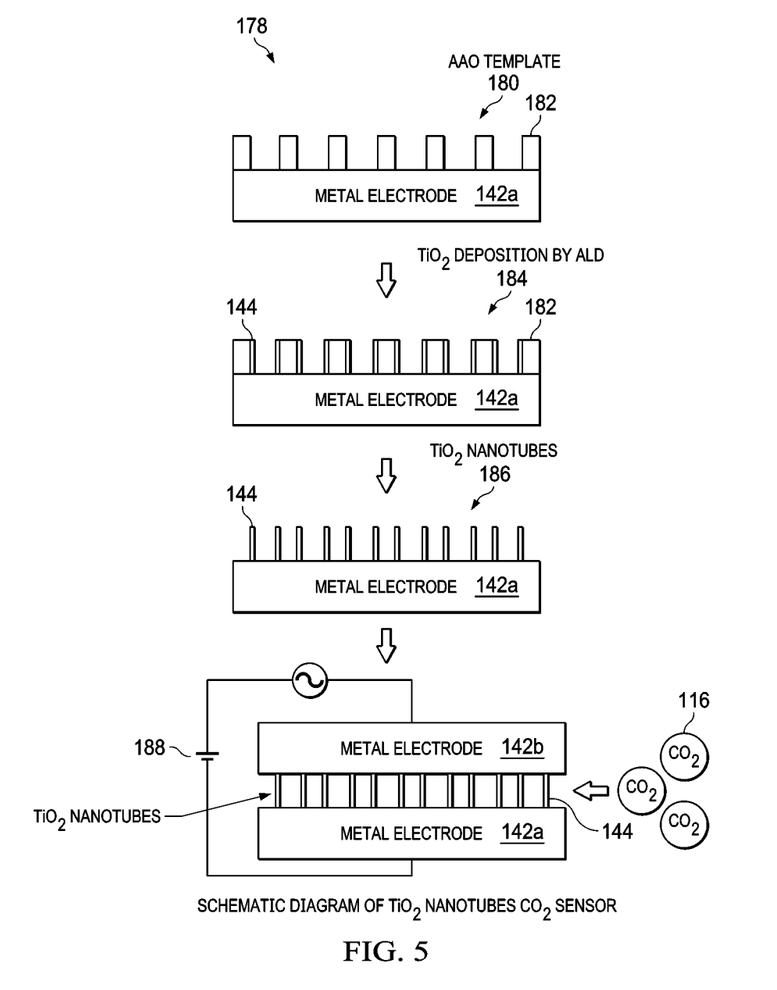
FIG. 5 is a schematic of a method for fabrication of sensor modules configuration shown in FIGS. 3A-3D.

FIG. 5 is a schematic illustrating a method 178 for fabricating sensor modules 136 configuration shown in FIGS. 3A-3D. At step 180, anodic aluminum oxide (AAO) membrane template 182 is attached on a first conductive electrode 142a (e.g., with commercially available super glue). AAO membranes are commercially available from Sigma-Aldrich Company (e.g., Whatman filter). At step 184, a growth of a plurality of $TiO_2$ nanotubes 144 is initiated inside the AAO template 182 using an atomic layer deposition (ALD) process. During the ALD process, a layer including the plurality of $TiO_2$ nanotubes is grown on the electrode substrate 142a by exposing its surface to alternating gaseous species (typically referred to as precursors). The precursors are not present simultaneously in the reactor, but they are inserted as a series of sequential, non-overlapping pulses. In each of these pulses, the plurality of $TiO_2$ nanotubes 144 reacts with the surface of the electrode 142a in a self-limiting way, so that the reaction terminates once all the reactive sites on the surface are consumed. The thickness of the plurality of $TiO_2$ nanotubes 144 is determined based on the number of cycles of the ALD disposition and the height of the plurality of $TiO_2$ nanotubes 144 is determined by the thickness of the AAO template 182. By varying the number of ALD cycles, the thickness and the height of the $TiO_2$ nanotubes 144 can be modified.

At step 186, once the ALD deposition is completed, the AAO template 182 is removed using chloroform. At step 188, a second conductive electrode 142b is attached to the plurality of $TiO_2$ nanotubes 144. Electrodes 142a and 142b are connected with an electric line to one another. The method 178 forms a sensor module 136 that in some examples, can be installed on a rollable surface (FIG. 1) and carried and installed at the enhanced oil recovery field. In other examples, the fabricated sensor module 136 can be installed on a drill rig 156 (FIG. 2) and used to detect and monitor carbon dioxide leakage in shallow wells that are located close to the carbon dioxide injection site. The operation principle of the sensor 140 is that when the plurality of $TiO_2$ nanotubes 144 react with carbon dioxide content 108 the depletion layer is increased and this increases the electrical resistance. Therefore, the change in electrical resistance is interpreted as carbon dioxide detection.

Figure 6:
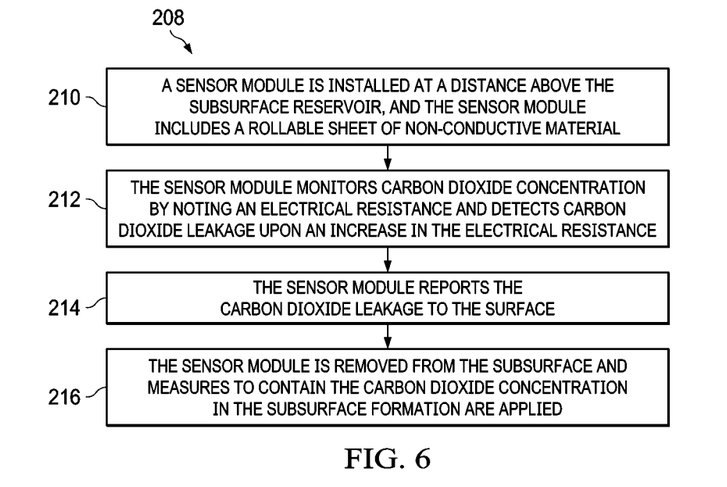
FIG. 6 is a flowchart of a method for deployment and use of a sensor module in a subsurface formation.

FIG. 6 is a flowchart of a method 208 for deployment and use of a sensor module 136 in a subsurface formation 100. In operation, a sensor module is installed at a distance above the subsurface reservoir, and the sensor module includes a rollable sheet of non-conductive material (210). The sensor module monitors carbon dioxide concentration by noting an electrical resistance and detects carbon dioxide leakage upon an increase in the electrical resistance (212). The sensor module reports the carbon dioxide leakage to the surface (214). The sensor module is removed from the subsurface and measures to retain the carbon dioxide concentration in the subsurface formation are applied (216).

Figure 7:
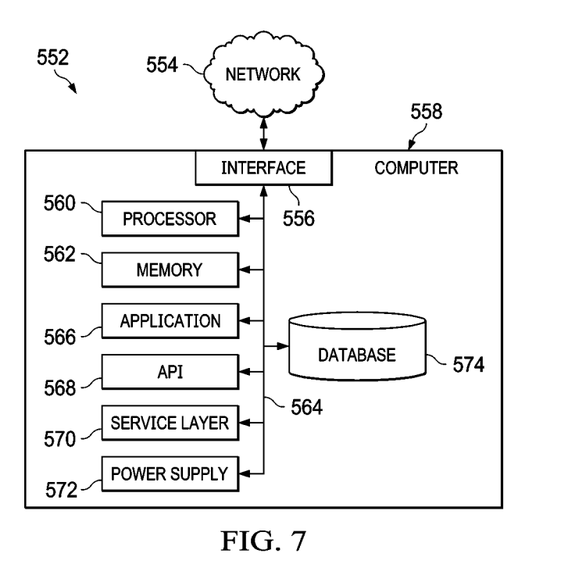
FIG. 7 is a block diagram of an example computer system.

FIG. 7 is a block diagram of an example computer system 552 used to provide computational functionalities associated with described algorithms, methods, functions, processes, flows, and procedures described in the present disclosure, according to some implementations of the present disclosure. The illustrated computer 558 is intended to encompass any computing device such as a server, a desktop computer, a laptop/notebook computer, a wireless data port, a smartphone, a personal data assistant (PDA), a tablet computing device, or one or more processors within these devices, including physical instances, virtual instances, or both. The computer 558 can include input devices such as keypads, keyboards, and touch screens that can accept user information. Also, the computer 558 can include output devices that can convey information associated with the operation of the computer 558 The information can include digital data, visual data, audio information, or a combination of information. The information can be presented in a graphical user interface (UI) (or GUI).

The computer 558 can serve in a role as a client, a network component, a server, a database, a persistency, or components of a computer system for performing the subject matter described in the present disclosure. The illustrated computer 558 is communicably coupled with a network 554. In some implementations, one or more components of the computer 558 can be configured to operate within different environments, including cloud-computing-based environments, local environments, global environments, and combinations of environments.

At a high level, the computer 558 is an electronic computing device operable to receive, transmit, process, store, and manage data and information associated with the described subject matter. According to some implementations, the computer 558 can also include, or be communicably coupled with, an application server, an email server, a web server, a caching server, a streaming data server, or a combination of servers.

The computer 558 can receive requests over network 554 from a client application (for example, executing on another computer 558). The computer 558 can respond to the received requests by processing the received requests using software applications. Requests can also be sent to the computer 558 from internal users (for example, from a command console), external (or third) parties, automated applications, entities, individuals, systems, and computers. Each of the components of the computer 558 can communicate using a system bus 564. In some implementations, any or all of the components of the computer 558, including hardware or software components, can interface with each other or the interface 556 (or a combination of both), over the system bus 564. Interfaces can use an application programming interface (API) 568, a service layer 570, or a combination of the API 568 and service layer 570. The API 568 can include specifications for routines, data structures, and object classes. The API 568 can be either computer-language independent or dependent. The API 568 can refer to a complete interface, a single function, or a set of APIs.

The service layer 570 can provide software services to the computer 558 and other components (whether illustrated or not) that are communicably coupled to the computer 558. The functionality of the computer 558 can be accessible for all service consumers using this service layer. Software services, such as those provided by the service layer 570, can provide reusable, defined functionalities through a defined interface. For example, the interface can be software written in JAVA, C++, or a language providing data in extensible markup language (XML) format. While illustrated as an integrated component of the computer 558, in alternative implementations, the API 568 or the service layer 570 can be stand-alone components in relation to other components of the computer 558 and other components communicably coupled to the computer 558. Moreover, any or all parts of the API 568 or the service layer 570 can be implemented as child or sub-modules of another software module, enterprise application, or hardware module without departing from the scope of the present disclosure.

The computer 558 includes an interface 556. Although illustrated as a single interface 556 in FIG. 7, two or more interfaces 556 can be used according to particular needs, desires, or particular implementations of the computer 558 and the described functionality. The interface 556 can be used by the computer 558 for communicating with other systems that are connected to the network 554 (whether illustrated or not) in a distributed environment. Generally, the interface 556 can include, or be implemented using, logic encoded in software or hardware (or a combination of software and hardware) operable to communicate with the network 554. More specifically, the interface 556 can include software supporting one or more communication protocols associated with communications. As such, the network 554 or the interface's hardware can be operable to communicate physical signals within and outside of the illustrated computer 558.

The computer 558 includes a processor 560. Although illustrated as a single processor 560 in FIG. 7, two or more processors 560 can be used according to particular needs, desires, or particular implementations of the computer 558 and the described functionality. Generally, the processor 560 can execute instructions and can manipulate data to perform the operations of the computer 558, including operations using algorithms, methods, functions, processes, flows, and procedures as described in the present disclosure.

The computer 558 also includes a database 574 that can hold data for the computer 558 and other components connected to the network 554 (whether illustrated or not). For example, database 574 can be an in-memory, conventional, or a database storing data consistent with the present disclosure. In some implementations, database 574 can be a combination of two or more different database types (for example, hybrid in-memory and conventional databases) according to particular needs, desires, or particular implementations of the computer 558 and the described functionality. Although illustrated as a single database 574 in FIG. 7, two or more databases (of the same, different, or combination of types) can be used according to particular needs, desires, or particular implementations of the computer 558 and the described functionality. While database 574 is illustrated as an internal component of the computer 558, in alternative implementations, database 574 can be external to the computer 558.

The computer 558 also includes a memory 562 that can hold data for the computer 558 or a combination of components connected to the network 554 (whether illustrated or not). Memory 562 can store any data consistent with the present disclosure. In some implementations, memory 562 can be a combination of two or more different types of memory (for example, a combination of semiconductor and magnetic storage) according to particular needs, desires, or particular implementations of the computer 558 and the described functionality. Although illustrated as a single memory 562 in FIG. 7, two or more memories 562 (of the same, different, or combination of types) can be used according to particular needs, desires, or particular implementations of the computer 558 and the described functionality. While memory 562 is illustrated as an internal component of the computer 558, in alternative implementations, memory 562 can be external to the computer 558.

The application 566 can be an algorithmic software engine providing functionality according to particular needs, desires, or particular implementations of the computer 558 and the described functionality. For example, application 566 can serve as one or more components, modules, or applications. Further, although illustrated as a single application 566, the application 566 can be implemented as multiple applications 566 on the computer 558. In addition, although illustrated as internal to the computer 558, in alternative implementations, the application 566 can be external to the computer 558.

The computer 558 can also include a power supply 572. The power supply 572 can include a rechargeable or non-rechargeable battery that can be configured to be either user- or non-user-replaceable. In some implementations, the power supply 572 can include power-conversion and management circuits, including recharging, standby, and power management functionalities. In some implementations, the power-supply 572 can include a power plug to allow the computer 558 to be plugged into a wall socket or a power source to, for example, power the computer 558 or recharge a rechargeable battery.

There can be any number of computers 558 associated with, or external to, a computer system containing computer 558, with each computer 558 communicating over network 554. Further, the terms "client," "user," and other appropriate terminology can be used interchangeably, as appropriate, without departing from the scope of the present disclosure. Moreover, the present disclosure contemplates that many users can use one computer 558 and one user can use multiple computers 558.

Implementations of the subject matter and the functional operations described in this specification can be implemented in digital electronic circuitry, intangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially-generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/–R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure. Accordingly, other embodiments are within the scope of the following claims.

What is claimed is:

1. A method for fabricating a sensor module for detecting carbon dioxide leakage from a subsurface reservoir, the method comprising:
   attaching an anodic aluminum oxide porous membrane onto a first conductive electrode to form an anodic aluminum oxide template;
   initiating growth of a plurality of $TiO_2$ nanotubes inside the anodic aluminum oxide template using an atomic layer deposition process;
   dissolving the anodic aluminum oxide porous membrane with a chloroform solution to remove the anodic aluminum oxide template from the first conductive electrode leaving the plurality of $TiO_2$ nanotubes on the first conductive electrode;
   attaching a second conductive electrode to the plurality of $TiO_2$ nanotubes;
   connecting the first and the second conductive electrodes with an electric line to form a sensor;

providing a rollable sheet of non-conductive material, the rollable sheet having a width between 50 cm and 2 m, a height between 50 cm and 2 m, and a thickness between 5 and 10 cm; and attaching a plurality of sensors to the rollable sheet of non-conductive material to form the sensor module.

2. The method of claim 1, wherein the sensor includes an electrical resistance sensor.

3. The method of claim 1, further comprising covering of each sensor from the plurality of sensors with a protective cover to prevent contamination.

4. A sensor module for detecting carbon dioxide leakage in a subsurface reservoir comprising:

a rollable sheet of non-conductive material with a rollable surface, wherein the rollable surface comprises a width between 50 cm and 2 m, a height between 50 cm and 2 m, and a thickness between 5 and 10 cm;

a plurality of sensors comprising a first conductive electrode, a second conductive electrode, and a plurality of $TiO_2$ nanotubes, and an electric line located between and connecting the first and the second conductive electrodes, wherein each of the sensors are fabricated by:

attaching an anodic aluminum oxide porous membrane onto the first conductive electrode to form an anodic aluminum oxide template;

initiating growth of a plurality of $TiO_2$ nanotubes inside the anodic aluminum oxide template using an atomic layer deposition process;

dissolving the anodic aluminum oxide porous membrane with a chloroform solution to remove the anodic aluminum oxide template from the first conductive electrode leaving the plurality of $TiO_2$ nanotubes on the first conductive electrode;

attaching the second conductive electrode to the plurality of $TiO_2$ nanotubes; and connecting the first and the second conductive electrodes with the electric line to form a sensor, and wherein each of the plurality of sensors is attached to the rollable sheet of non-conductive material; and a communication device communicably connected to each sensor from the plurality of sensors.

5. The sensor module of claim 4, wherein the rollable sheet comprises rubber.

6. The sensor module of claim 4, further comprising a protective cover to prevent contamination of each sensor from the plurality of sensors before and after sensing.

7. The sensor module of claim 6, wherein the protective cover comprises rubber.

8. The sensor module of claim 4, wherein each sensor from the plurality of sensors has a maximum dimension between 5 and 10 cm, and a thickness between 1 and 2 cm.

9. The sensor module of claim 8, wherein each sensor from the plurality of sensors has a circular shape, and the maximum dimension is a diameter.

10. The sensor module of claim 4, wherein the plurality of sensors are attached to the rollable sheet and are arranged in an array.

11. The sensor module of claim 4, wherein the plurality of sensors are attached to the rollable sheet and arranged in a parallel configuration.

12. A method for detecting a carbon dioxide leakage from a subsurface reservoir to a ground surface, the method comprising:

deploying a sensor module above the subsurface reservoir, the sensor module comprising a rollable sheet of non-conductive material, wherein the sensor module is fabricated by:

attaching an anodic aluminum oxide porous membrane onto a first conductive electrode to form an anodic aluminum oxide template;

initiating growth of a plurality of $TiO_2$ nanotubes inside the anodic aluminum oxide template using an atomic layer deposition process;

dissolving the anodic aluminum oxide porous membrane with a chloroform solution to remove the anodic aluminum oxide template from the first conductive electrode leaving the plurality of $TiO_2$ nanotubes on the first conductive electrode;

attaching a second conductive electrode to the plurality of $TiO_2$ nanotubes; and connecting the first and the second conductive electrodes with an electric line to form a sensor;

monitoring a carbon dioxide concentration by noting an electrical resistance using the sensor module;

detecting the carbon dioxide leakage upon an increase in the electrical resistance between the first conductive electrode and the second conductive electrode across the plurality of $TiO_2$ nanotubes;

reporting the carbon dioxide leakage to the ground surface using the sensor module; and removing the sensor module from the subsurface reservoir.

13. The method of claim 12, wherein deploying the sensor module comprises unrolling the sensor module.

14. The method of claim 12, further comprises placing the sensor module on a ground surface.

15. The method of claim 12, wherein the sensor module comprises a plurality of sensors attached to the rollable sheet.

16. The method of claim 15, wherein each sensor from the plurality of sensors comprises an electrical resistance sensor.

17. The method of claim 15, further comprises covering of each sensor from the plurality of sensors before and after sensing with a protective cover to prevent contamination.

* * * * *